United States Patent

Stockton

[11] Patent Number: 5,859,536
[45] Date of Patent: Jan. 12, 1999

[54] MOISTURE SENSOR HAVING LOW SENSITIVITY TO CONDUCTANCE CHANGES

[75] Inventor: Paul Stockton, Portland, N. Dak.

[73] Assignee: Oliver Haugen, Mayville, N. Dak.

[21] Appl. No.: 780,686

[22] Filed: Jan. 8, 1997

[51] Int. Cl.⁶ .......................... G01R 27/26; G01N 27/22
[52] U.S. Cl. .......................... 324/664; 324/667; 324/690; 73/73; 239/64
[58] Field of Search .................................. 324/663, 664, 324/667, 668, 674, 675, 677, 681, 682, 686, 689, 690, 694, 696; 73/73; 340/604; 239/63, 64, 70; 137/78.2, 78.3, 624.11, 624.12

[56] References Cited

U.S. PATENT DOCUMENTS

| | | |
|---|---|---|
| Re. 31,023 | 9/1982 | Hall, III ........................................ 47/1 |
| 3,821,967 | 7/1974 | Sturman et al. .................... 137/624.15 |
| 3,874,590 | 4/1975 | Gibson ....................................... 239/63 |
| 3,882,383 | 5/1975 | Matlin ...................................... 324/696 |
| 3,989,066 | 11/1976 | Sturman et al. ..................... 137/624.2 |
| 4,015,366 | 4/1977 | Hall, III ......................................... 47/1 |
| 4,197,866 | 4/1980 | Neal ............................................ 137/1 |
| 4,396,149 | 8/1983 | Hirsch ....................................... 239/63 |
| 4,531,087 | 7/1985 | Larson ..................................... 324/696 |
| 4,545,396 | 10/1985 | Miller et al. ............................ 137/78.3 |
| 4,546,645 | 10/1985 | Delmulle et al. ....................... 324/690 |
| 4,549,314 | 10/1985 | Masuda et al. .......................... 455/618 |
| 4,567,563 | 1/1986 | Hirsch ...................................... 364/420 |
| 4,655,076 | 4/1987 | Weihe et al. .................................. 73/73 |
| 4,683,904 | 8/1987 | Iltis ......................................... 324/667 |
| 4,801,865 | 1/1989 | Miller et al. ............................. 324/696 |
| 4,909,070 | 3/1990 | Smith ............................................ 73/73 |
| 4,929,885 | 5/1990 | Dishman .................................. 324/664 |
| 4,931,775 | 6/1990 | Sheriff ...................................... 340/604 |
| 4,952,868 | 8/1990 | Scherer, III ............................. 324/664 |
| 5,005,005 | 4/1991 | Brossia et al. ........................... 340/604 |
| 5,021,939 | 6/1991 | Pulgiese ................................... 364/143 |
| 5,060,859 | 10/1991 | Bancroft ..................................... 239/64 |
| 5,142,901 | 9/1992 | Nagawa et al. .............................. 73/73 |
| 5,148,985 | 9/1992 | Bancroft .................................... 239/64 |
| 5,260,666 | 11/1993 | Dishman et al. ........................ 324/664 |
| 5,341,673 | 8/1994 | Burns et al. .................................. 73/73 |
| 5,373,738 | 12/1994 | Abkowitz et al. .................... 73/335.04 |
| 5,430,384 | 7/1995 | Hocker ..................................... 324/694 |
| 5,445,178 | 8/1995 | Feuer ......................................... 137/1 |
| 5,450,015 | 9/1995 | Mastico et al. .......................... 324/672 |
| 5,463,377 | 10/1995 | Kronberg ................................. 340/605 |

*Primary Examiner*—Diep N. Do
*Attorney, Agent, or Firm*—Duane, Morris & Heckscher LLP

[57] ABSTRACT

A sensing device includes a pair of sensing electrodes disposed within a medium and a circuit connected to the sensing electrodes via impedance matching networks for producing an output signal which varies in response to a capacitive change in the medium. The circuit includes a first circuit portion including the sensing electrodes and a second circuit portion including the oscillator. The first and second circuit portions are tuned to match their impedance for more accurately measuring the capacitive changes.

20 Claims, 3 Drawing Sheets

MOISTURE SENSOR HAVING LOW SENSITIVITY TO CONDUCTANCE CHANGES

FIELDS OF THE INVENTION

This invention relates to sensing devices for measuring the presence of liquids in porous media, and more particularly, to moisture sensing devices for minimizing conductance errors in moisture due to contaminants and additives, such as salt and fertilizer.

BACKGROUND OF THE INVENTION

The demand for water in irrigation systems in this country has been relentless. Increasing demand for water has forced us to replace grass and vegetation with concrete, brick and rock. Wet land farming is being substituted for dry land farming, and conservation of all kinds has been encouraged to help replenish water supplies and underground springs. Technology which is capable of conserving water is constantly being sought, but there has been very little improvement, even with the advent of sophisticated new electronics.

Soil moisture detection has been used for monitoring and evaluating construction sites, landscape sites, mining operations, forest areas, flood control areas, and farming districts. The ability to determine the moisture content of granular, or packed powder media is also important in the manufacturing of cement, plaster, gravel or brick. Moisture content measurements are additionally important to sampling grain water content, field water content, and storage water content. Direct probe measurements of produce, such as growing potatoes, can provide valuable information related to moisture content, temperature, and ionic conductance activity which relate to chemical changes during the growth cycle.

Moisture sensors are often used in conjunction with sprinkler controls to regulate the flow of water in proportion to the watering needs of grass and plants. For low dielectric media, such as soil, it has been recognized that the moisture content affects the overall dielectric content of the media to a detectable degree. It is widely known that water has a relatively high dielectric constant of about 80, while dry soil typically has a much lower dielectric constant of approximately 5 or 6. The water content of soil is therefore one of the major contributors to the overall dielectric constant of the soil.

There have been many moisture sensors which have been developed for reacting to the dielectric properties of a soil sample. One popular technology employs capacitance test probes such as those disclosed in U.S. Pat. Nos. 5,445,178, 4,929,885 and 4,545,396, which are hereby incorporated by reference. No capacitive devices were found that are not strongly susceptible to effects of conductance. These devices use conductive surfaces of a probe which are imbedded in the soil. The soil is used as a dielectric, which forms a capacitor with the conductive surfaces. The capacitance provided by one of these emersed probe surfaces is used as part of an LC oscillator circuit having an oscillation frequency which varies when the dielectric property of the soil sample changes due to moisture conditions. While such devices have had limited success in measuring water content, some have had difficulty in accurately deciphering moisture contents in soils having varying degrees of salinity i.e., Salinity affects conductivity.

Early water sensing devices were not very accurate since they rarely measured the soil's capacitance without significant errors caused by temperature dependencies, or high conductivity. Saline-tainted soil and other, more unique soil types, have a definite significant effect on the measurement. The simplified electrical analogy of the medium is that of impedance, a parallel resistor and capacitor combination. Moisture sensing circuitry is therefor based on the measurement of the conductance of the resistive component and/or the reactance of the capacitive. The varying conductivity properties of the medium tends to adversely interfere with the ability of LC and RC oscillator, or frequency oriented measurement systems to accurately indicate the moisture content of the medium. Both components, created by the impedance of the medium tend to affect the oscillation frequency of some circuits, rendering it almost impossible to separate the effects of the medium's conductivity properties from those related to the medium's dielectric properties. Errors due to conductivity are further complicated by its inherent temperature dependence.

If the medium to be monitored is agricultural soil, it may contain various non-soil components, such as fertilizer, buffers, salts and the like. The complex electrical analogy of a soil/water medium results in an inaccurate indication of the moisture concentration if the circuitry is designed to produce a water content measurement based on a corresponding change in the dielectric of the medium as a function of a change in water content in the medium. Very simply, the ability of the circuitry to measure water content by the change in dielectric method, must provide evidence that the circuit is designed to isolate, remove, or be insensitive to conductivity.

Accordingly, a significant need exists for an inexpensive, water monitoring system which is capable of being sensitive to soil water content, electrical conductance and temperature even if the soil contains materials which greatly affect dielectric properties.

SUMMARY OF THE INVENTION

The present invention provides moisture sensing devices and methods for measuring the moisture content of a medium. The device includes a pair of sensing electrodes disposed within a sample of the medium. Impedance matching networks, such as a π-impedance matching networks, driven at a frequency which is sensitive to capacitance changes in the medium is connected to the electrodes for producing an output signal which is indicative of a moisture content of the sample. This measurement circuit does not involve the detection of a change in frequency. The frequency of the oscillator is constant. Two impedance matching networks connect the oscillator to the probes by terminating the output impedance of the oscillator's output driver to a complex impedance at the probe. The terminating impedance is designed to have a very low conductance and high reactance.

This technique (comprising the water measurement by method of the change in dielectric constant), provides high sensitivity to a change in reactance in the medium, and very low sensitivity to changes of conductance in the medium.

Accordingly, this invention provides tuned circuit portions for matching the low impedance output of the excitation frequency source to the low impedance of the output of the matching network connected to the soil. Correct tuning of these networks causes an effective low impedance to be seen at the output of the network, where the sensing electrodes are attached, whether or not, the probes are immersed in a measurement medium. This low electrode resistance causes the output of the network to be minimally affected by non-reactive loads. The matched networks of these sensing devices are, therefore, rather insensitive to conductance in the soil due to saline and other chemical effects.

In further embodiments of this invention, methods for sensing the moisture content of the medium are provided. The methods provide a sensing device having a pair of electrodes which incorporates an impedance matching circuit for producing an output signal which is indicative of a moisture content of the medium even with high moisture contents. This is accomplished by using a two stage impedance matching network to match the oscillator's source impedance to that of the medium where a change in the capacitance of the medium de-tunes the matching network creating a highly sensitive measurement to the capacitive change in the medium. Further developments of this invention are discussed below.

BRIEF DESCRIPTION OF THE DRAWINGS

The accompanying drawings illustrate a complete embodiment of the invention according a preferred mode for the practical application of the principles thereof, and in which.

DETAILED DESCRIPTION OF THE INVENTION

Figure 1:
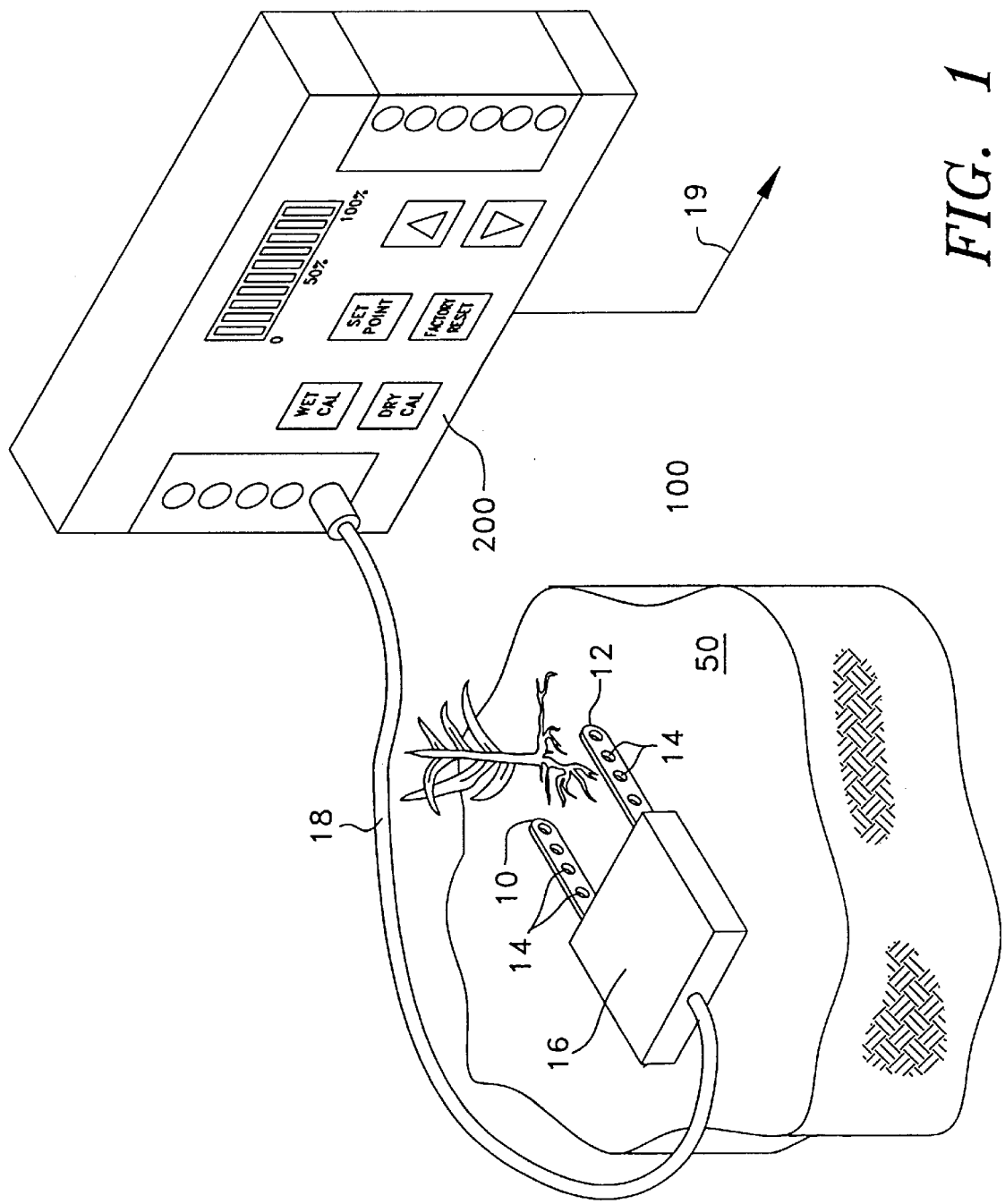
FIG. 1 is a diagrammatic view of the preferred sensor and control panel of this invention.
Figure 2:
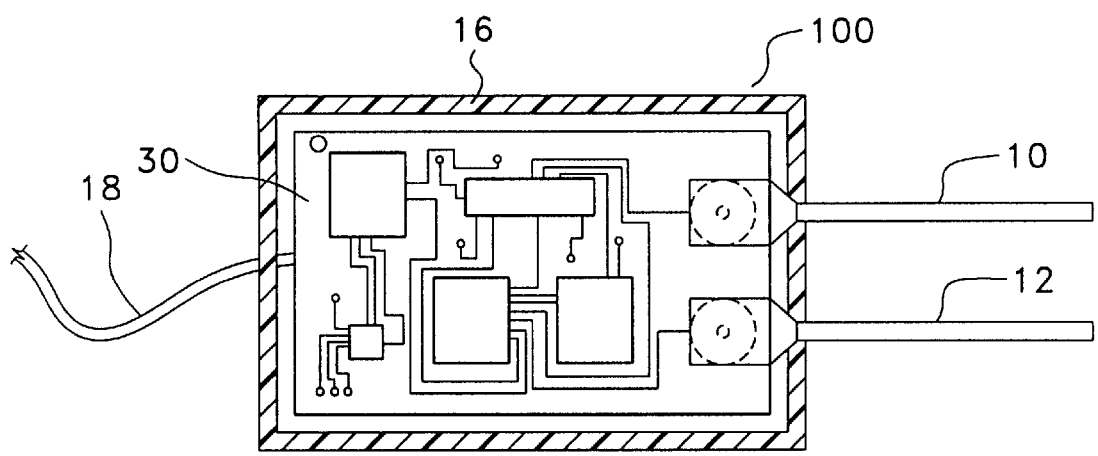
FIG. 2 is a cross-sectional top view of the preferred sensing device of this invention.
Figure 3:
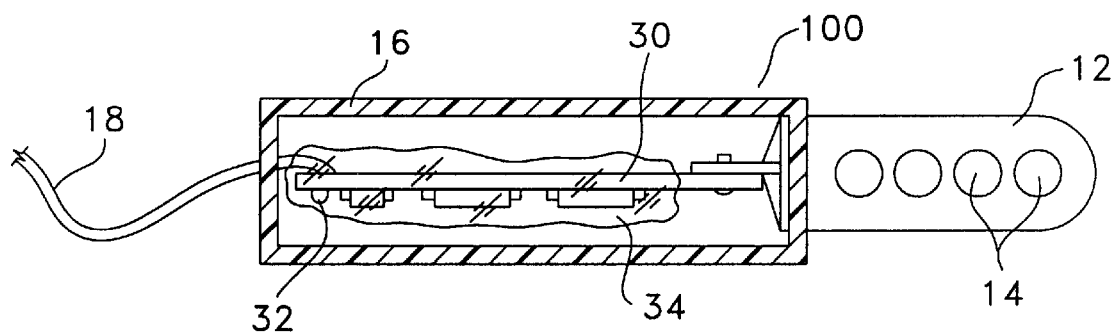
FIG. 3 is a cross-sectional side view of the preferred sensing device of FIG. 2.

With reference to the figures, and more particularly to FIGS. 1–3 thereof, there is shown a preferred sensor 100 equipped with a pair of sensing electrodes 10 and 12 which are inserted into soil 50. The soil sample located between the sensing electrodes 10 and 12 acts as a dielectric. The dielectric constant of this sample can vary with the amount of moisture, temperature and degree of impurities present. The sensor 100 includes a polymer housing 16 and a cable 18 which connects one or more sensors to a control panel 200. Alternatively the sensor 100 and control panel 200 can communicate by wireless infrared, microwave, or radio signals, for example. The control panel 200 can be equipped with a microprocessor and various calibration circuitry for addressing many moisture and soil conditions. Control panel 200 has an output which routes through cable 19 to a sprinkler control panel, for example, which in turn, controls hubs for sprinkler heads, etc.

The preferred sensor 100, contains a printed circuit board 30, shown in FIGS. 2 and 3, electrically mounted to the sensing electrodes 10 and 12. The sensor also embodies a microprocessor performing measurement and communications functions. The sensing electrodes 10 and 12 contain apertures 14 which hold soil tightly so that contractions of the soil in cold temperatures do not permit the soil to disengage from their conductive surfaces. The sensing electrodes 10 and 12 are preferably made from a corrosion resistant, electrically conductive polymer, but other materials such as bronze, brass, nickel, stainless steel or copper can be used.

Preferred conductive polymers can include a resin which has been filled with an electrically conducting powder, such as carbon, graphite or metal flake. One preferred conductive polymer is polyurethane with a loading of about 25–50 wt % graphite or carbon.

The printed circuit board 30 of the sensor 100 is protected within a polymeric housing 16, which is made of a corrosion resistant and ultra-violet light resistant material, such as polyurethane. In order to prevent shorting of the elements on the circuit board 30, the conductive surfaces can be further encapsulated in a water-tight material such as silicone or glass-filled epoxy 34. A LED 32 is provided for presenting an observable flashing indication when a wet or dry calibration has been verified.

Assuming the sensor is in a soil medium with a water content which is at field capacity, the module will perform a wet calibration and store this value internally. The auto-wet calibration will be performed because the factory preset wet calibration is intentionally set below normal soil at field capacity. A manual wet calibration can be performed at any time by temporarily grounding the wet calibration wire, located on a six pin connector of the control panel 200. The LED 32, located beneath the polymeric housing 16 will flash verifying that the calibration has been performed. Automatic wet calibrations are performed whenever the module reads a value higher than the stored wet calibration value. When this happens, the new value replaces the old calibration value.

A manual dry calibration can be performed by temporarily grounding the dry calibration pin or wire, located on the six pin connector of the control panel 200. The LED 32 also verifies this calibration. If a dry calibration is manually performed when the soil is oven dry, and, a manual wet calibration is performed at a matrix potential of 10 centibars (field capacity (FC) as defined by the Soil Conservation Service) the output range of 0–100% represents a reproducible data set of volumetric soil water content. When a dry calibration is performed at a water content equivalent to the permanent wilting point (PWP) for a specific vegetative species in a specific soil type and texture, the output range of 0–100% represents the percent of available water for that vegetation. This is extremely valuable if one is only concerned with a singular species of vegetation such as the turf on golf courses. Automatic dry calibrations are performed by the interface modules whenever the sensor sends a signal representing a condition drier than the internal dry calibration value. If the unit is in the "manual" mode, automatic calibrations are not performed.

The preferred control panel 200 contains a microprocessor control for accommodating these manual dry, manual wet and factory reset calibrations, as well as the automatic dry and wet calibrations. It can be equipped to produce a digital (RS 232, RS 422, RS 485, or the newer EIA/TIA-232E static protected specification serial interface, which are hereby incorporated by reference) or analog output. It communicates with the sensor via RS-232 or RS485, translates the information, and makes this information readable by the user via serial communications or optionally, analog output. It is preferably powered by 12 volts of current at 80 mA for the control panel 200, and about 150 mA for both the sensor and control panel 200.

The preferred measurements or data produced by the sensor 100 of this invention are water content, electrical conductivity, and temperature. The water content is a measurement of the moisture of any medium in units of volume, or by electrical terminology, such as dielectric constant, capacitive reactance or capacitance. The electric conductivity is the measurement of the conductivity, "G", of any medium. Current activity is also represented by its reciprocal function, resistivity, "R". The temperature of the medium is also an important consideration, since it effects electrical properties. Temperature adjustments are made by the microprocessor in the control panel 200.

This invention prefers to use two different circuit designs for calculating water content and electrical conductivity. The water content circuitry responds to the dielectric constant of the medium being measured. Electronically, it functions as an impedance matching network which matches the impedance of the signal source oscillator to the impedance of the medium. As used herein, the terms "match" or "matches" mean that these impedance measurements are less than about 10% apart, and preferably less than about 1% apart with the medium at a field capacity, wet condition. Impedance is known to contain three components: resistance, capacitive reactance and inductive reactance. The sensor 100 is designed to focus upon the resistance and capacitive reactance of the medium. The sensing electrodes 10 and 12 are placed within the medium to be measured and the circuitry mounted on circuit board 30 is attached to the low impedance end of the impedance matching network, namely a 5 volt DC source driven by an oscillator having a clock frequency of about 40–80 MHz as shown substantially in FIG. 4. This high frequency oscillator is set to a frequency sufficiently high enough to measure the calculated range of dielectric of the soil for dry and wet conditions. This range is nominally 4 to 100 picofarads respectively. The circuitry is thereafter tuned so that the conductive component of the impedance of the medium measured at the sensing electrodes 11 and 12 to be low. The measured signal is the rectified RF signal at the probe.

The unique design feature of this invention is that the impedance matching network has been specifically designed to be relatively insensitive to resistance, or conductance, of the medium when a moisture content measurement is taken. This has been accomplished while, at the same time, permitting the circuitry to be very sensitive to dielectric constant changes or capacitive changes in the medium. As the dielectric constant in the medium changes with the presence of water, the water content of the medium is accurately measured. Because of the unique arrangement of this impedance matching circuitry, reduces the effects of conductance, errors associated with conductive moisture measurement methods, are minimized, allowing this invention to reject the effects of ions present in the medium, such as salt ions.

The conductance measurement, providing temperature and volume corrections are made, can be used to monitor levels of fertilizer, or other chemical additives.

Figure 4:
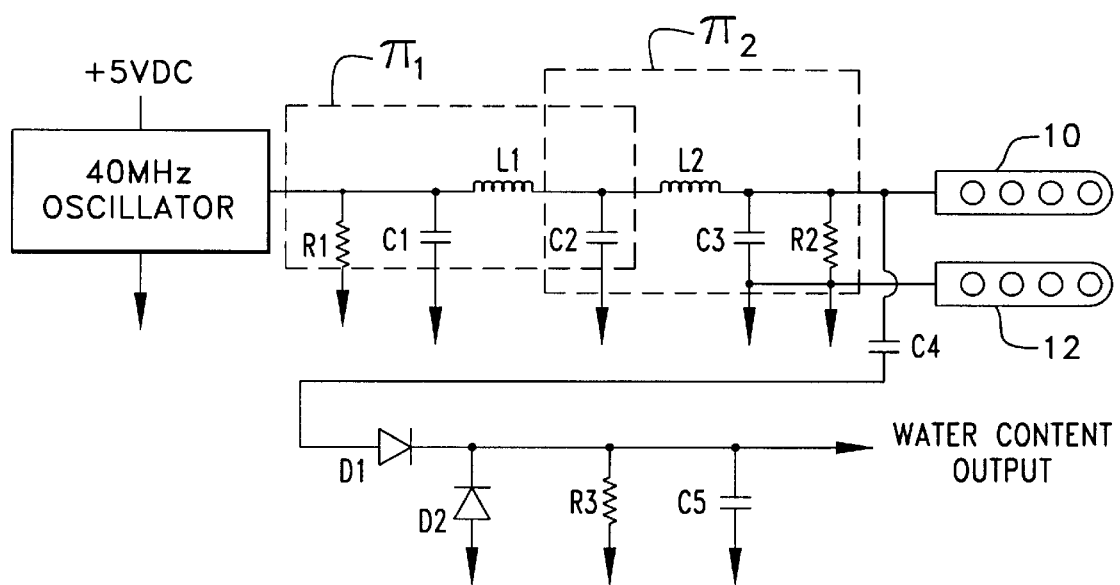
FIG. 4 is a preferred tuned matching network of the preferred sensor of this invention.

The circuit diagram shown in FIG. 4 provides a preferred impedance matching circuit which is useful in connection with this invention. The preferred design represents a tuned $\pi$ network. The oscillator provides a 40 MHz signal to the first $\pi$ network, $\pi 1$ (R1, C1, L1, C2). C2, L2, C3, R2 and the probe capacitance form the second $\pi$ network, $\pi 2$. The values of C1, C2, C3, L1 and L2 are set to tune each $\pi$ section. R1 represents the source load resistor.

The input impedance at the junction of C1 and L1 matches the impedance of the output of the oscillator. The output impedance located at the junction of L2 and C3 and the capacitance of the probe represented by electrodes 10 and 12 in a soil sample are the output impedance adjusted to cause an output reactive component of about 100 ohms under a volumetric water content field capacity condition. C2 is adjusted to set the output voltage a the probe to a low voltage. Properly tuned, these networks drive a low impedance which increases as increased capacitive reactance detunes the second $\pi$ network. An increase in dielectric occurs as an increase of capacitive reactance caused by the increased capacitance in the soil due to increasing water content. The functions are similar and mathematically tend to produce a tangential function by the controller's processor. However, this is not necessary for irrigation purposes.

C4 couples the signal to the rectifier D1. Diodes D1 and D2 rectify the varying amplitude of the 40 MHz constant frequency signal. C5 integrates the rectified signal, and R3 is the discharge path for C5, determining the response time. The response time can be extremely fast.

The output of this circuit can be digitized by any of a multitude of low cost embedded microprocessors. The conductance circuitry, not shown, couples to the electrodes 10 and 12 through a RF choke. The conductance signal, along with a common temperature signal are also read by the microprocessor. This microprocessor performs and stores calibration values and temperature corrections as needed. It also sends the processed data to a high-end irrigation controller via a variety of industry standard serial interface protocols.

The present invention also employs conductivity measurements, which can be measured independently from the capacitance sensing, and processed by the control panel 200 for various purposes. Electrical conductivity is used in monitoring or controlling the application of fertilizer in advanced irrigation control systems. It is also useful in measuring the salinity and leaching processing of soils in remote or non-irrigated areas, and the infiltration or migration of hazardous materials, waste water contamination, feed lot contamination migration, agricultural chemical fertilization, and herbicide or insecticide contamination, to name a few.

From the foregoing, it can be realized that this invention provides improved water sensors and sensing methods which minimize the errors associated with conductance, by minimizing the effects of conductance of the medium to be measured with an oscillating load current. These methods and devices provide highly accurate measurements of water content of soil and other media. Although various embodiments have been illustrated, this is for the purpose of describing but not limiting the invention. Various modifications, which will become apparent to those skilled in the art, are within the scope of this invention described in the attached claims.

What is claimed is:

1. A moisture sensing device for measuring the moisture content of a medium, comprising:

a pair of sensing electrodes disposed within said medium;

a circuit connected to said pair of sensing electrodes for producing an output signal which varies in response to a change in the dielectric constant of said medium, said circuit comprising an oscillator providing a signal having a constant frequency;

an electrode circuit portion including said sensing electrodes and said medium, said electrode circuit portion having an output resistance sufficiently low to be insensitive to a chance in conductance of the medium, and an output reactance which varies substantially in response to the change in the dielectric constant of said medium, said electrode circuit portion providing the output signal; and a matching circuit portion, coupled between the oscillator and the electrode circuit portion, the impedance of the matching circuit portion approximately matching the impedance of the electrode circuit portion at the constant frequency, if the medium has a predetermined condition, wherein a measurable mismatch occurs when the dielectric constant of said medium varies from the dielectric constant at the predetermined condition, indicating a change in moisture content of said medium.

2. The moisture sensing device of claim 1 wherein said approximate impedance matching is within about 10%.

3. The moisture sensing device of claim 2 wherein said circuit comprises a π-matching circuit.

4. The moisture sensing device of claim 1 wherein said oscillator comprises an excitation frequency of about 30–80 MHz.

5. The moisture sensing device of claim 1 wherein said oscillator generates a excitation frequency of at least about 40 MHz.

6. The moisture sensing device of claim 1 wherein said approximate impedance matching is within about 1% and said circuit can measure capacitance from about 4 to about 100 pf.

7. The moisture sensing device of claim 6 wherein said circuit is sensitive to changes in capacitive reactance and is substantially less sensitive to conductance in said medium.

8. The moisture sensing device of claim 1 further comprising microprocessor means for calculating said dielectric changes, and a conductance change of said medium, based on the output signal.

9. The moisture sensing device of claim 8 wherein said microprocessor means produces an electrical output used in regulating a sprinkler or irrigation device.

10. A method of measuring a water content of a medium, comprising:

providing a moisture sensing device including a pair of sensing electrodes disposed within said medium and an impedance matching circuit which includes a conductance in parallel with the sensing electrodes, said impedance matching circuit having an output resistance sufficiently low to be insensitive to a change in conductance of the medium, and an output reactance which varies substantially in response to the change in the dielectric constant of said medium;

operating an oscillator at a constant frequency, the oscillator being coupled to the sensing device by the impedance matching circuit;

disposing said electrodes in said medium;

measuring an output signal of the impedance matching circuit; and detecting a mismatch in said impedance matching circuit, based on the output signal of the sensing electrodes, if a moisture content of said medium varies over time, the mismatch indicating a change in the dielectric constant of said medium.

11. The method of claim 10 further comprising driving said oscillator at a frequency of at least about 30 MHz.

12. The method of claim 11 wherein said impedance matching circuit comprises a π-matching circuit, a Y-matching circuit or a reciprocal π-matching circuit.

13. The method of claim 10 wherein said sensing electrodes are disposed within a soil having a capacitance range of about 4–100 pf.

14. The method of claim 10 wherein said moisture content measurement is derived principally from said change in dielectric constant of the medium.

15. A moisture sensor comprising:

a polymeric housing;

a printed circuit board mounted within said housing;

a pair of sensing electrodes electrically connected to said printed circuit board and disposed through said housing into a medium to be measured;

said printed circuit board comprising:

an oscillator which operates at a constant frequency; and a circuit connecting the sensing electrodes to the oscillator, said circuit having an output resistance sufficiently low to be insensitive to a change in conductance of the medium, and an output reactance which varies substantially in response to the change in the dielectric constant of said medium, the circuit providing an output signal that indicates a matched condition at the constant frequency when the medium has a predetermined dielectric constant, the output signal indicating a measurable mismatch when the dielectric constant of said medium varies from the dielectric constant at the predetermined condition, indicating a change in moisture content of said medium.

16. The sensor of claim 15 further comprising a polymeric sealant disposed over said printed circuit board.

17. The sensor of claim 15 wherein said sensing electrodes comprise a conductive polymer.

18. The sensor of claim 15 wherein said circuit comprises a π-matching circuit.

19. The sensor of claim 15 wherein said oscillator is driven at an excitation frequency of greater than about 30 MHz.

20. The sensor of claim 15 in combination with a microprocessor control means for regulating an irrigation flow in response to capacitive changes measured by said sensor.

* * * * *